US006281153B1

(12) United States Patent
Becke et al.

(10) Patent No.: US 6,281,153 B1
(45) Date of Patent: Aug. 28, 2001

(54) CATALYSTS BASED ON FULVENE METAL COMPLEXES

(75) Inventors: Sigurd Becke, Rösrath; Rüdiger Beckhaus, Oldenburg, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/463,244

(22) PCT Filed: Jul. 17, 1998

(86) PCT No.: PCT/EP98/04459

§ 371 Date: Jan. 21, 2000

§ 102(e) Date: Jan. 21, 2000

(87) PCT Pub. No.: WO99/06448

PCT Pub. Date: Feb. 11, 1999

(30) Foreign Application Priority Data

Jul. 30, 1997 (DE) .............................................. 197 32 804

(51) Int. Cl.[7] ................................ B01J 31/22; B01J 31/38
(52) U.S. Cl. ........................ 502/104; 502/102; 502/117; 502/152; 526/160; 526/943
(58) Field of Search .................................... 502/102, 104, 502/117, 152; 526/160, 943

(56) References Cited

U.S. PATENT DOCUMENTS

| | | | |
|---|---|---|---|
| 4,542,199 | 9/1985 | Kaminsky et al. | 526/160 |
| 4,808,561 | 2/1989 | Welborn, Jr. | 502/104 |
| 4,871,705 | 10/1989 | Hoel | 502/117 |
| 4,912,075 | 3/1990 | Chang | 502/107 |
| 4,914,253 | 4/1990 | Chang | 585/523 |
| 5,008,228 | 4/1991 | Chang | 502/111 |
| 5,145,819 | 9/1992 | Winter et al. | 502/117 |
| 5,276,208 | 1/1994 | Winter et al. | 556/53 |
| 5,278,119 | 1/1994 | Turner et al. | 502/155 |
| 5,324,800 | 6/1994 | Welborn, Jr. et al. | 526/160 |
| 5,334,677 | 8/1994 | Razavi et al. | 526/114 |
| 5,407,884 | 4/1995 | Turner et al. | 502/155 |
| 5,483,014 | 1/1996 | Turner et al. | 526/113 |
| 5,580,939 | 12/1996 | Ewen et al. | 526/127 |
| 5,633,394 | 5/1997 | Welborn, Jr. et al. | 556/11 |
| 6,054,405 | * 4/2000 | Wenzel | 502/104 |

FOREIGN PATENT DOCUMENTS

| | | |
|---|---|---|
| 277004 | 8/1988 | (EP) . |
| 427697 | 5/1996 | (EP) . |
| 468537 | 11/1996 | (EP) . |
| 500944 | 10/1998 | (EP) . |

OTHER PUBLICATIONS

Organometallics (month unavailable) 1987, 6, pp. 232–241, Laurel E. Schock et al, "Intramolecular Thermolytic C–H Activation Processes. Solid–State Structural Characterization of a Mononuclear $\eta^6$–$Me_4C_5CH_2$ Zirconium Complex and a Mechanistic Study of Its Formation from $(Me_5C_5)_2Zr(C_6H_5)_2$".

J. Am. Chem. Soc., (month unavailable) 1986, pp. 7410–7411, Richard F. Jordan et al "Ethylene Polymerization by a Cationic Dicyclopentadienylzirconium (IV) Alkyl Complex".

JACS (month unavailable) 1972, vol. 42, pp. 1219–1238, John E. Bercaw, et al "Titanocene as an Intermediate in Reactions Involving Molecular Hydrogen and Nitrogen".

J. Am. Soc. (month unavailable) 1988, 110, pp. 7701–7715, Laurel E. Schock et al "Organometallic Thermochemistry. Metal Hydrocarbyl, Hydride, Halide, Carbonyl, Amide, and Alkoxide Bond Enthalpy Relationships and Their Implications in Pentamethylcyclopentadienyl and Cyclopentadienyl Complexes of Zirconium and Hafnium".

Periodic Table of the Elements [N. N. Greenwood, A. Earnshaw, Chemie der Elemente, VCH 1990], "Periodensystem der Elemente—mit Elektronenkonfigurationen im Grundzustand".

* cited by examiner

Primary Examiner—David W. Wu
Assistant Examiner—Caixia Lu
(74) Attorney, Agent, or Firm—Joseph C. Gil; Noland J. Cheung

(57) ABSTRACT

This invention relates to a catalyst system based on fulvene metal complexes as well as their use for the polymerization of unsaturated compounds, in particular for the polymerization and copolymerization of olefins and/or dienes.

8 Claims, No Drawings

CATALYSTS BASED ON FULVENE METAL COMPLEXES

FIELD OF THE INVENTION

The present invention relates to a catalyst system based on fulvene metal complexes as well as their use for the polymerization of unsaturated compounds, in particular for the polymerization and copolymerization of olefins and/or dienes.

BACKGROUND OF THE INVENTION

The use of cyclopentadienyl metal complexes, in particular the use of metallocene complexes in a mixture with activating co-catalysts, preferably alumoxanes (MAO), for the polymerization of olefins and diolefins has been known for a long time (e.g. EP-A 129 368, 347 128, 347 129, 69 951, 351 392, 485 821, 485 823).

The metallocenes have proven to be highly effective, specific catalysts in the polymerization of in particular olefins. In order, therefore, to increase the activity, selectivity, control of the micro-structure, the molecular weights and the molecular weight distribution, a large number of novel metallocene catalysts or metallocene catalyst systems have been developed in recent years for the polymerization of olefinic compounds.

The MAO-based catalyst systems described above have serious drawbacks, however, as will be explained in detail below. Firstly, aluminoxanes, in particular MAO, can be manufactured with high reproducibility neither in situ nor during preforming. MAO is a mixture of various aluminum alkyl-containing species, which are present in equilibrium with each other. The number and the structure of the aluminum compounds occurring in MAO is not defined precisely. The polymerization of olefins with catalyst systems that contain MAO is therefore not always reproducible. Moreover, MAO is not storable over long periods and its composition changes under thermal stress. A major disadvantage is the high surplus of MAO which is required for the activation of metallocenes. The large MAO/metallocene ratio is an essential pre-requisite for obtaining high catalyst activities. This results in a critical process drawback, as the aluminum compound has to be separated from the polymer during the working up. MAO is furthermore a cost-determining factor. High MAO surpluses are uneconomic for industrial application.

In order to circumvent these drawbacks, alumoxane-free polymerization catalysts have been developed in recent years. For example, Jordan et al report in J. Am. Chem. Soc., Vol. 108 (1986), 7410 on a cationic zirconocene-methyl complex which possesses tetraphenyl borate as counter-ion and polymerizes ethylene into methylene chloride. In EP-A 277 003 and EP-A 277 004 ionic metallocenes are described which are produced by the reaction of metallocenes with ionizing reagents. In EP-A 468 537 catalysts of ionic structure are described which are obtained by reacting metallocene-dialkyl compounds with tetrakis (pentafluorophenyl)boron compounds. The ionic metallocenes are suitable as catalysts for the polymerization of olefins. A disadvantage is however the great sensitivity of the catalysts to impurities such as e.g. humidity and oxygen. Measures therefore have to be taken during the performance of polymerizations to guarantee as great a purity of the monomers and solvents used as possible. This is very complicated technically and expensive.

In order to overcome these drawbacks, there are described in EP-A 427 697 and in WO 92/01723 processes for the polymerization of olefins in which a combination of metallocene dichlorides with aluminum alkyls and tetrakis (pentafluorophenyl)boron compounds is used as a catalyst system. The aluminum alkyl compounds on the one hand serve as alkylation agents of the metallocene component and on the other function as scavengers in order to protect the active catalyst species against impurities.

The methods corresponding to the prior art for preparing the cationic metallocenes have the drawback, however, that the cationizing reagents, e.g. tetrakis(pentafluorophenyl) boron compounds, are difficult to synthesize in some cases and their use is cost-intensive.

According to Bercaw et al., JACS (1972), 94, 1219, there is obtained by thermolysis of bis($\eta^5$-pentamethylcyclopentadienyl)titanium dimethyl the fulvene complex ($\eta^6$-2,3,4,5-tetramethylcyclopentadienyl-1-methylene)($\eta^5$-pentamethylcyclopenta-dienyl)-titanium methyl. Nothing is known about the polymerization activity of this complex. In T. J. Marks et al., JACS (1988), 110, 7701 the thermolysis of pentamethyl-cyclopentadienyl complexes of zirconium and hafnium is described. By thermolysis of bis($\eta^5$-pentamethyl-cyclopentadienyl)zirconium diphenyl the fulvene complex ($\eta^6$-2,3,4,5-tetramethylcyclopentadienyl-1-methylene)($\eta^5$-pentamethylcyclopentadienyl)-zirconium phenyl is obtained. This compound is not polymerization-active on its own.

SUMMARY OF THE INVENTION

The object therefore existed of finding a catalyst system which prevents the above-mentioned drawbacks. In addition, processes based on aluminoxane-free metallocene systems were to be developed.

It has now been found, surprisingly, that catalyst systems based on fulvene metal complexes are particularly highly suitable for the objects set.

The present invention therefore provides a catalyst system consisting of a) a fulvene metal complex with the formula

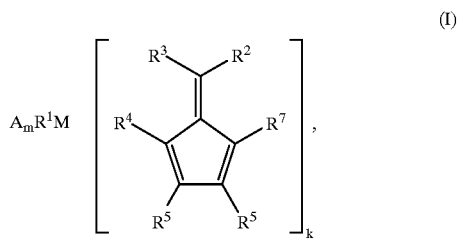

(I)

in which

M is a metal from the group IIIb, IVb, Vb, VIb or of the lanthanides or of the actinides of the Periodic Table of the Elements [N. N. Greenwood, A. Earnshaw, Chemie der Elemente, VCH 1990], A signifies an optionally uni- or multi-bridged anionic ligand, $R^1$, $R^2$, $R^3$, $R^4$, $R^5$, $R^6$, and $R^7$ are identical or different and stand for hydrogen, halogen, a cyano group, a $C_1$ to $C_{20}$ alkyl group, a $C_1$ to $C_{10}$ fluoroalkyl group, a $C_6$ to $C_{10}$ fluoroaryl group, a $C_1$ to $C_{10}$ alkoxy group, a $C_6$ to $C_{20}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a $C_2$ to $C_{10}$ alkinyl group, a silyl group optionally substituted by $C_1$ to $C_{10}$ hydrocarbon groups or $R^1$, $R^2$, $R^3$, $R^4$, $R^5$, $R^6$, and $R^7$ form respectively together with the atoms linking them one or more aliphatic or aromatic ring systems, which can contain one or more hetero atoms (O, N, S) and have 5 to 10 carbon atoms, m signifies 0, 1, 2 or 3 and k is 1, 2 or 3 and the sum of m+k comes to 1 to 5 as a function of the oxidation state of M and b) an aluminoxane- and boron-free Lewis acid suitable for activating the metal complex a), wherein the molar ratio of component a) to component b) lies in the range of 1:0.1 to 1:10,000, preferably 1:1 to 1:1,000.

The synthesis of the fulvene metal complexes of formula (1) is known and described for example in T. J. Marks et al., Organometallics 1987, 6, 232–241.

DETAILED DESCRIPTION OF THE INVENTION

The present invention further provides a process for producing a catalyst system, characterized in that a mixture of an aluminoxane- and boron-free Lewis acid suitable for activation and a metal complex of formula (II)

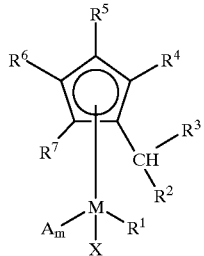

in which

M, A, $R^1$ to $R^7$ have the above meanings and

X stands for hydrogen, halogen, a $C_1$ to $C_{30}$ alkyl group, a $C_6$ to $C_{10}$ aryl group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a $C_2$ to $C_{10}$ alkinyl group, an optionally substituted silyl group, is treated thermally in a suitable reaction medium.

The thermal treatment takes place in the temperature range from 60° C. to 250° C., preferably from 90° C. to 150° C. The duration of the thermal treatment lies in the range from 1 minute to 20 hours, preferably in the range from 15 minutes to 120 minutes. Suitable reaction media are for example aromatic hydrocarbons, such as benzene or toluene, or aliphatic hydrocarbons, such as hexane, heptane, octane, cyclohexane or mixtures of the various hydrocarbons. The thermal treatment is not carried out in the presence of an olefin or diolefin. The molar ratio of the Lewis acid to the metal complex of formula (II) lies in the range from 1:0.1 to 1:10,000, preferably 1:1 to 1:1,000.

There are considered as fulvene metal complexes of formula (I) in particular those in which M is a metal of the group IVb, Vb or of the lanthanides of the Periodic Table of the Elements, A is an allyl group of the formula $C_3R^6 5$, where $R^6$ has the same signification as $R^1$ to $R^6$ in formula (I), a halide, F, Cl, Br, I, a sulfonate of the formula $O_3SR^6$, an amide of the formula $NR^6{}_2$, a pyrazolate of the formula $N_2C_3R^7{}_3$ with $R^7$ for hydrogen or a $C_1$–$C_{10}$ alkyl group, a pyrazolyl borate of the formula $R^6B(N_2C_3R^7{}_3)_3$, an alcoholate or phenolate of the formula $OR^6$, a siloxane of the formula $OSiR^6{}_3$, a thiolate of the formula $SR^6$, an acetyl acetonate of the formula $(R^1CO)_2CR^6$, a diimine of the formula $(R^1N=CR^6)_2$, a cyclopentadienyl of the formula $C_5H_qR^6{}_{5-q}$ with q for 0, 1, 2, 3, 4, 5, an indenyl of the formula $C_9H_{7-r}R^6{}_r$ with r for 0, 1, 2, 3, 4, 5, 6, 7, a fluorenyl of the formula $C_{13}H_{9-s}R^6{}_s$ with s for 0, 1, 2, 3, 4, 5, 6, 7, 8, 9 and a $C_1$ to $C_{30}$ alkyl group, a $C_6$ to $C_{10}$ aryl group, and a $C_7$ to $C_{40}$ alkylaryl group, $R^1$ to $R^5$ and $R^6$ stand for a $C_1$–$C_{30}$ alkyl group, a $C_6$–$C_{10}$ aryl group, a $C_7$–$C_{40}$ alkylaryl group, in particular for hydrogen, methyl, ethyl, n-propyl, isopropyl, n-butyl, isobutyl, tert.-butyl, phenyl, methylphenyl, cyclohexyl and benzyl, m and k possess the aforementioned signification.

Quite particularly preferred are fuilvene metal complexes of formula (1), in which M stands for titanium, zirconium, hafnium, vanadium, niobium and tantalum, A stands for bis(trimethylsilyl)amide, dimethylamide, diethylamide, diisopropylamide, 2,6-di-tert.-butyl-4-methyl phenolate, cyclopentadienyl, methylcyclopentadienyl, benzyl-cyclopentadienyl, n-butylcyclopentadienyl, pentamethylcyclopentadienyl, tetramethyl-cyclopentadienyl, 2,4,7-trimethiylcyclopentadienyl, dimethylcyclopentadienyl, indenyl, 2-methylindenyl, 2-methyl-4,5-benzoindenyl, 2-methyl-4-phenylindenyl, fluorenyl or 9-methyl-fluorenyl.

The specified formula (I) for the fulvene metal complexes is to be regarded as a formal description of the bonding relationships and represents an example of a structural variant. As is known to the skilled man, the bonding relationships of the metal complex are inter alia dependent on the central atom, on the oxidation state and on the substituents of the fulvene ligand.

There are considered as Lewis acids the co-catalysts known in the field of Ziegler-Natta catalysis, such as e.g. compounds of aluminiuLIm. magnesium or zinc. Suitable as Lewis acids are in particular trialkylaluminum compounds, such as trimethylaluminum, triethylaluminum, triisobutylaluminum, triisoctylaluminum, and in addition dialkylaluminum compounds such as diisobutylaluminum hydride, diisobutylaluminum fluoride and diethylaluminum chloride, and also substituted triaryl-aluminum compounds, such as tris(pentafluorophenyl)aluminum, as well as ionic compounds which contain as anion tetrakis (pentafluorophenyl)aluminate, such as triphenyl-methyl-tetrakis(pentafluorophenyl) aluminate, as well as N,N-dimethylanilinium-tetrakis-(pentafluorophenyl) aluminate. Further examples of suitable Lewis acids are dialkyl compounds of zinc or magnesium, such as dimethyl zinc, diethyl zinc, diisobutyl zinc, butylethyl magnesium, dibutyl magnesium, as well as dihexyl magnesium.

It is naturally possible to use the co-catalysts in a mixture with each other.

The present invention further provides the use of the novel catalyst system for the polymerization of unsaturated compounds, in particular of olefins and dienes. By polymerization is understood both the homo- and the copolymerization of the above-mentioned unsaturated compounds. In particular use is made for the polymerization of $C_2$–$C_{10}$ alkenes, such as ethylene, propylene, 1-butene, 1-pentene, 1-hexene, 1-octene, isobutylene and arylalkenes, such as styrene. There are used as dienes in particular: conjugated dienes, such as 1,3-butadiene, isoprene, 1,3-pentadiene, and non-conjugated dienes, such as 1,4-hexadiene, 1,5-heptadiene, 5,7-dimethyl-1,6-octadiene, 4-vinyl-1-cyclohexene, 5-ethylidene-2-norbornene, 5-vinyl-2-norbornene and dicyclopentadiene.

The catalysts according to the invention are suitable for the production of rubbers based on copolymers of ethylene with one or more of the above-mentioned α-olefins and the above-mentioned dienes. In addition, the catalyst system according to the invention is suitable for the polymerization of cycloolefins such as norbornene, cyclopentene, cyclohexene, cyclooctane, and the copolymerization of cycloolefins with ethylene or α-olefins.

The polymerization can be carried out in liquid phase, in the presence or absence of an inert solvent, or in the gas phase. As solvents are suitable aromatic hydrocarbons, such as benzene and/or toluene, or aliphatic hydrocarbons, such as propane, hexane, heptane, octane, isobutane, cyclohexane or mixtures of the various hydrocarbons.

It is possible to use the catalyst system according to the invention applied to a support. There can be mentioned as suitable support materials e.g.: inorganic or organic polymeric supports, such as silica gel, zeolites, carbon black, activated carbon, aluminum oxide, polystyrene and polypropylene.

The catalyst system according to the invention can further be applied to the support materials in a conventional manner. Methods for the supporting of catalyst systems are for example described in U.S. Pat. Nos. 4,808,561, 4,912,075, 5,008,228 and 4,914,253.

The polymerization is carried out in general at pressures of 1 to 1,000, preferably 1 to 100 bar, and temperatures of −100 to +250° C., preferably 0 to +150° C. The polymerization can be carried out in conventional reactors, continuously or discontinuously.

The invention will be described in detail by means of the following examples.

General details: Production and handling of organometallic compounds took place with the exclusion of air and humidity under argon protection (Schlenk method). All required solvents were absolutized prior to use by boiling for several hours over a suitable desiccant and subsequent distillation under argon.

The synthesis of the compounds of formula (I) and formula (II) took place in accordance with T. J. Marks et al., *Organometallics* 6 (1987) 232–241. The compounds were characterized with $^1$H-NMR, $^{13}$C-NMR and mass spectroscopy.

Abbreviations:
Cp*: $C_5(CH_3)_5$
Cp"": $C_5(CH_3)_4H$
Ind: $C_9H_7$
$F_v$: $C_5(CH_3)_4$=$CH_2$
$F_v$"": $C_5(CH_3)_3H$=$CH_2$
Ph: $C_6H_5$
PhLi: phenyl lithium
HV: high vacuum
RT: room temperature A. Synthesis of the compounds of formula (II)

EXAMPLE 1

Bis($\eta^5$-pentamethylcyclopentadienyl) zirconiumdiphenyl, [Cp*$_2$ZrPh$_2$]

3.62 g (8.37 mmol) of bis($\eta^5$-pentamethylcyclopentadienyl)zirconium dichloride were suspended in 60 ml of diethyl ether, the yellow-white suspension obtained was cooled to −78° C. and 13.90 ml (25.0 mmol) of PhLi were added dropwise. The whole was then heated to RT and stirred overnight. The beige suspension was evaporated to dryness under HV and the residue absorbed in 40 ml hexane. This suspension was filtered and the resulting red solution half evaporated, during which a white solid precipitated. The suspension was cooled to −20° C. for further crystallization. The solution was decanted and the remaining product dried under HV. 2.94 g (68%) was obtained.

EXAMPLE 2

Bis($\eta^5$-tetramethylcyclopentadienyl) zirconiumdiphenyl, [(Cp"")$_2$ZrPh$_2$]

2.06 g (5.05 mmol) of bis($\eta^5$-tetramethylcyclopentadienyl)zirconium dichloride were suspended in 60 ml ether, the yellow-white suspension obtained was cooled to −78° C. and 8.48 ml (15.27 mmol) of PhLi were slowly added dropwise. The whole was then heated to RT and stirred overnight. The orange suspension formed was evaporated to dryness under HV and the residue absorbed in 40 ml hexane. Filtering took place and the filtrate was half evaporated, during which an orange-yellow solid precipitated. The suspension was cooled to −20° C. for further crystallisation. The orange, needle-shaped crystals were isolated and dried under HV. 1.38 g (56%) was obtained.

EXAMPLE 3

($\eta^5$-pentamethylcyclopentadienyl)($\eta^5$-indenyl) zirconium-diphenyl, [(Cp*)(Ind)ZrPh$_2$]

640 mg (1.55 mmol) of ($\eta^5$-pentamethylcyclopentadienyl)($\eta^5$-indenyl)zirconium-dichloride were suspended in 40 ml ether. 2.41 ml (4.34 mmol) of PhLi were added dropwise at −78° C., heated to RT and stirred overnight. The brownish yellow suspension was evaporated under HV, the residue absorbed in n-hexane and filtered. The resulting clear yellow-brown solution was half evaporated under HV and cooled to −20° C. for crystallization. The light beige solid thereby precipitated was isolated and dried under HV. 345 mg (45%) were obtained.

B. Synthesis of the compounds of formula (I)

EXAMPLE 4

($\eta^6$-(2,3,4,5-tetramethylcyclopentadienyl-1-methylene)($\eta^5$-pentamethylcyclo-penta-dienyl) zirconiumphenyl, [(Cp*)(Fv)ZrPh]

4.20 g (8.14 mmol) of Cp*$_2$ZrPh$_2$ produced according to Example 1 were dissolved in 20 ml toluene. The yellow solution was heated to 110° C. over 6 h, during which it turned a dark red color. After cooling, the solvent was removed under HV. The bright red residue was absorbed in a little hexane and crystallized at −20° C. The mother liquor was decanted and the bright red crystals were dried under HV. 2.56 g (72%) of a red crystalline solid were obtained.

EXAMPLE 5

($\eta^6$-trimethylcyclopentadienyl-methylene)($\eta^5$-tetramethylcyclopentadienyl)-zirconiumphenyl, [(Cp"")(Fv"") ZrPh]

900 mg (1.85 mmol) of Cp""$_2$ZrPh$_2$ produced according to Example 2 were dissolved in 20 ml toluene. This orange solution was heated to 100° C. over 2 h, during which it turned a dark red colour. After cooling, the solvent was removed under HV. The residue was absorbed in a little n-hexane and crystallized at −20° C. The mother liquor was decanted from the red crystals and after drying a reddish brown solid was obtained, which according to NMR data consists of two isomers in the ratio 92: 8. 363 mg (48%) were obtained.

EXAMPLE 6

($\eta^6$-2,3,4,5-tetramethylcyclopentadienyl-1-methylene)($\eta^5$-indenyl)zirconiumphenyl, [(Fv)(Ind)ZrPh]

A solution of 120 mg (0.24 mmol) of Cp*IndZrPh$_2$ produced according to Example 3 was heated to 100° C. over 1 h in toluene, during which a color change from yellow to red occurred. After cooling, the solvent was removed under HV. The residue was absorbed in a little hexane and crystallized at −20° C. The mother liquor was decanted from the red crystals and dried under HV. 68 mg (67%) were obtained.

C. Polymerization Examples

EXAMPLE 7

Production of the Catalyst Solution 20.5 mg (40 μmol) of [Cp*$_2$ZrPh$_2$] from Example 1 were dissolved in 16 ml toluene. 4 ml of a 1 molar triisobutylaluminum (TIBA) solution in toluene were then added and heated at 100° C. for 60 minutes, during which the initially colorless solution turned a bright yellow color.

Polymerization of Ethylene 100 ml of toluene and 0.5 ml of a 1 molar solution of TIBA in toluene were introduced into a 250 ml glass reactor and stirred for 10 min. Ethylene was then introduced into the solution continuously with a gas delivery tube at a pressure of 1.1 bar. The polymerization was started by the addition of 1 ml of the catalyst solution. After polymerization for a period of 15 min at a temperature of 40° C. and an ethylene pressure of 1.1 bar the reaction was terminated by the addition of 10 ml of methanol, the polymer obtained filtered off, washed with acetone and dried in a vacuum-drying oven. 2.02 g of polyethylene were obtained.

COMPARATIVE EXAMPLE

Example 7 was repeated, with the difference that instead of the catalyst solution 1 ml of a solution of 17.7 mg (34 μmol) of [Cp*$_2$ZrPh$_2$] in 16.6 ml toluene without thermal pre-treatment was used. No polymer was obtained.

EXAMPLE 8

Production of the Catalyst Solution 23.7 mg (54 μmol) of [(Cp*)(Fv)ZrPh] from Example 4 were dissolved in 27 ml toluene.

Polymerization of Ethylene

The polymerization from Example 7 was repeated, with the difference that instead of TIBA, 0.5 mmol tris (2,4,4-trimethyl-pentyl)aluminum (TIOA) was introduced and the polymerization was started by the addition of 0.5 ml of the catalyst solution. 2.59 g of polyethylene were obtained.

EXAMPLE 9

Polymerization of Ethylene 2 l of toluene and 2 ml of TIBA were placed in a 6 l autoclave and stirred for 10 min. 1 ml of the catalyst solution from Example 8 was then added. The polymerization took place at 40° C. at an ethylene pressure of 10 bar. After a polymerization time of 30 minutes the autoclave was depressurized, the operation terminated with 1 l of methanol, the precipitated polymer deposit filtered off, washed with acetone and dried in a vacuum-drying oven. 27.9 g of highly crystalline polyethylene with a melting point of 150° C. according to DSC measurement were obtained.

EXAMPLE 10

Production of the Catalyst Solution 11.9 mg (24.4 μmol) of [(Cp'''')$_2$ZrPh$_2$] from Example 2 were dissolved in 10 ml toluene. 2.5 ml of a 1 molar triisobutylaluminum (TIBA) solution in toluene were then added and heated at 100° C. for 60 minutes, during which the initially colorless solution turned a clear yellow color.

Copolymerization of Ethylene and 1-hexene 100 ml of toluene, 0.5 ml of a 1 molar solution of TIBA in toluene and 2.5 ml 1-hexene were introduced into a 250 ml glass reactor and stirred for 10 min. Ethylene was then introduced into the solution continuously with a gas delivery tube at a pressure of 1.1 bar. The polymerization was started by the addition of 1 ml of the catalyst solution. After polymerization for a period of 15 min at a temperature of 40° C. and an ethylene pressure of 1.1 bar the reaction was terminated by the addition of 10 ml of methanol, the polymer obtained filtered off, washed with acetone and dried in a vacuum-drying oven. 1.6 g of an ethylene/1-hexene copolymer was obtained.

EXAMPLE 11

Production of the Catalyst Solution 15 mg (36.6 μmol) of [(Cp'''')(Fv'''')ZrPh] from Example 5 were dissolved in 36.6 ml toluene.

Copolymerization of Ethylene and Propylene 500 ml toluene and 1 ml triisobutylaluminum were introduced into a 1.4 l steel autoclave, which was fitted with a mechanical stirrer, manometer, temperature sensor, a temperature control device, a catalyst transfer tube and monomer metering devices for ethylene and propylene, and stirred for 10 min. 58 g of propylene were then added. The internal temperature was set to 40° C. with a thermostat. Ethylene was then added until the pressure inside the reactor rose to 4 bar. The polymerization was started by the addition of 2 ml of the catalyst solution and ethylene was added continuously so that the internal pressure at 40° C. was a constant 4 bar. After a polymerization time of 1 hour the polymerization was terminated with a 1% HCl solution in methanol, stirring took place for 10 min and the polymer was then precipitated with methanol. The polymer so obtained was washed with methanol, isolated and dried under vacuum for 20 h at 60° C., in the course of which 22.7 g of copolymer were obtained. The IR spectroscopic determination of the composition of the copolymer showed an incorporation of 86.4% ethylene and 13.6% propylene. A glass transition temperature of −29° C. was determined with the DSC method.

EXAMPLE 13

Production of the Catalyst Solution 13.6 mg (32.6 μmol) of [(Fv)(Ind)ZrPh] from Example 6 were dissolved in 32.6 ml toluene.

Terpolymerization of Ethylene, Propylene and 5-ethylidene-2-norbornene 500 ml toluene and 1 ml TIBA were introduced into a 1.4 l steel autoclave, which was fitted with a mechanical stirrer, manometer, temperature sensor, a temperature control device, a catalyst transfer tube and monomer metering devices for ethylene and propylene. 54 g of propylene and 5 ml of 5-ethylidene-2-norbornene were then added. The internal temperature was set to 40° C. with a thermostat. Ethylene was then added until the pressure inside the reactor rose to 4 bar. The polymerization was started by the addition of 5 ml of the catalyst solution and ethylene was added continuously so that the internal pressure at 40° C. was a constant 4 bar. After a polymerization time of 1 hour the autoclave was depressurized and the polymerization solution mixed with a 0.1 wt % hexane solution Vulkanox BKF, stirring took place for 10 min and the polymer was then precipitated with methanol. The polymer so obtained was isolated and dried under vacuum for 20 h at 60° C., in the course of which 89.7 g of terpolymer were obtained. The IR spectroscopic determination of the composition of the terpolymer showed an incorporation of 75.2% ethylene, 24.3% propylene and 0.5% ENB. A glass transition temperature of −37° C. was determined with the DSC method.

What is claimed is:

1. A process for producing a fulvene metal complex containing catalyst system comprising the step of thermally treating in a suitable reaction medium, a mixture of an aluminoxane- and boron-free Lewis acid suitable for activation and a metal complex of formula (II)

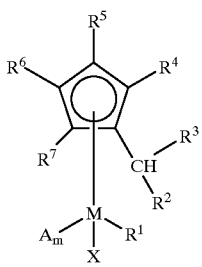

wherein

M is a metal cation from the group IIIb, IVb, Vb, VIb or of the lanthanides or of the actinides of the Periodic Table of the Elements [N. N. Greenwood, A. Earnshaw, Chemie der Elements, VCH 1990], A signifies an optionally uni- or multi-bridged anionic ligand, $R^1$, $R^2$, $R^3$, $R^4$, $R^5$, $R^6$, and $R^7$ are identical or different and stand for hydrogen, halogen, a cyano group, a $C_1$ to $C_{20}$ alkyl group, a $C_1$ to $C_{10}$ fluoroalkyl group, a $C_6$ to $C_{10}$ fluoroaryl group, a $C_1$ to $C_{10}$ alkoxy group, a $C_6$ to $C_{20}$ ayryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a $C_2$ to $C_{10}$ alkinyl group, an optionally substituted silyl group or form respectively together with the atoms linking them one or more ring systems, which can contain one or more hetero atoms, X stands for hydrogen, halogen, a $C_1$ to $C_{30}$ alkyl group, a $C_6$ to $C_{10}$ aryl group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a $C_2$ to $C_{10}$ alkinyl group, and an optionally silyl group.

2. Process according to claim 1, wherein the thermal treatment takes place in the temperature range from 60° C. to 250° C.

3. Process according to claim 1, characterized in that the period of the thermal treatment is in the range from 1 minute to 20 hours.

4. Process according to one of claim 1, wherein the thermal treatment is carried out in an aliphatic or aromatic solvent.

5. Process according to one of claim 1, wherein the thermal treatment does not take place in the presence of an olefin or diolefin.

6. A process according to claim 1, wherein the thermal treatment takes place in the temperature range from 90° C. to 150° C.

7. A process according to claim 1, wherein the period of the thermal treatment is in the range from 15 minutes to 6 hours.

8. A process according to claim 1, wherein said molar ration of component (a) to component (b) lies in the range of 1:1 to 1:1,000.

* * * * *